United States Patent [19]

Carter

[11] Patent Number: 4,692,545
[45] Date of Patent: Sep. 8, 1987

[54] METHOD FOR PREPARATION OF MERCAPTOBENZOATES

[75] Inventor: Charles G. Carter, Columbia, Md.

[73] Assignee: Stauffer Chemical Company, Westport, Conn.

[21] Appl. No.: 940,997

[22] Filed: Dec. 12, 1986

[51] Int. Cl.$^4$ .......................................... C07C 149/40
[52] U.S. Cl. .................................................. 560/18
[58] Field of Search ........................................ 560/18

[56] References Cited

U.S. PATENT DOCUMENTS

| | | | |
|---|---|---|---|
| 3,663,615 | 5/1972 | Zielger | 564/80 |
| 3,729,508 | 4/1973 | Zielger | 560/18 |
| 3,867,433 | 2/1975 | Shen | 562/427 |

OTHER PUBLICATIONS

Cogolli, J. Org. Chem., 44, pp. 2636–2642, (1979).

Primary Examiner—Michael L. Shippen
Attorney, Agent, or Firm—Joel G. Ackerman

[57] ABSTRACT

A method of preparing compounds of the formula

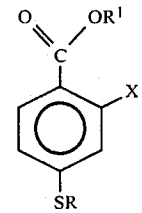

wherein R is alkyl, alkenyl, benzyl or aromatic, R$^1$ is alkyl and X is halogen or nitro comprising reacting a compound of the formula

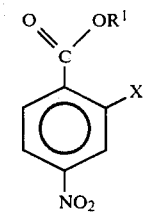

wherein R$^1$ and X are defined as above with a mercaptan having the formula R—SH in the presence of an inorganic base and a polar aprotic solvent.

10 Claims, No Drawings

METHOD FOR PREPARATION OF MERCAPTOBENZOATES

Compounds of the type

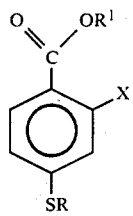

wherein $R^1$ is alkyl, R is alkyl, alkenyl, benzyl or aryl and X is halogen or nitro are useful intermediates in the synthesis of pesticides and pharmaceutical compounds. The carboxylic acids corresponding to these intermediates have been produced by various methods, including the displacement of a halogenated benzoic acid by a mercaptan in the presence of a base in an alcohol solvent to give a mercaptobenzoic acid, as described in U.S. Pat. No. 3,867,433. These methods are characterized by low yields or are limited to benzoates that are substituted at the 3-position by a strong electron-attracting group.

SUMMARY OF THE INVENTION

When an alkyl 4-nitro-2-substituted benzoate is reacted with a mercaptan in the presence of an inorganic base and a polar aprotic solvent the nitro group at the 4-position can be selectively displaced under mild conditions to give a high yield of an alkyl 4-alkylthio-2-substituted benzoate.

DESCRIPTION OF THE INVENTION

The process of this invention allows the selective displacement of the nitro group of an alkyl 4-nitro-2-substituted benzoate in the presence of an inorganic base and a polar aprotic solvent to prepare an alkyl 4-alkylthio-2-substituted benzoate. The resulting benzoate can be converted to the corresponding benzoic acid via conventional methods, with an overall yield of up to 99.67% of the benzoic acid based on the starting nitrobenzoate.

According to this invention alkyl 4-alkylthio-2-substituted benzoates can be prepared by reacting a compound of the formula

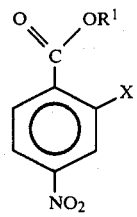

in which $R^1$ is alkyl and X is either halogen or nitro with a mercaptan in the presence of an inorganic base such as potassium carbonate, sodium carbonate, sodium hydride, trisodium phosphate, or tripotassium phosphate. A polar aprotic solvent such as acetone, methyl ethyl ketone, acetonitrile, dimethylformamide, N-methylpyrrolidone, dimethylacetamide or methyl isopropyl ketone and other such organic solvents inert to nucleophilic addition can be used. Mercaptans which are useful in this reaction have the formula R—SH in which R is alkyl, alkenyl, benzyl or aryl. The term "alkyl" includes both straight and branched chain saturated acyclic hydrocarbyl moieties and generally includes moieties having from 1 to 8 carbon atoms, preferably from 1 to 3. The term "alkenyl" includes both straight and branched chain unsaturated acyclic hydrocarbyl moieties and generally includes moieties having from 2 to 8 carbon atoms, preferably from 2 to 3. The term "aryl" includes phenyl and substituted phenyl. The term "halogen" includes chlorine and bromine.

The reaction is preferably run at a temperature from about 0° to about 160° C., more preferably from about 20° to about 70° C. The reaction can be run at subatmospheric to super-atmospheric pressure, preferably at atmospheric pressure. Preferred bases are trisodium phosphate, tripotassium phosphate, sodium carbonate and potassium carbonate, more preferably sodium carbonate and potassium carbonate, most preferably potassium carbonate.

The process of this invention can be better understood by reference to the following examples.

EXAMPLE I

Preparation of Ethyl 2-Nitro-4-methylthiobenzoate

To a 3-necked, round-bottom flask fitted with condenser and gas inlet, 104 grams (g), 0.752 mole (m) of potassium carbonate and 300 milliliters (ml) of acetone were added. While the mixture was stirring, 33.8 g (0.705 m) of mthyl mercaptan was introduced via subsurface addition followed by addition of 112.8 g (0.47 m) of ethyl 2,4-dinitrobenzoate. The mixture was stirred ten minutes and allowed to stand overnight at room temperature. The mixture was then evaporated under reduced pressure; extracted with ethyl acetate, washed with water followed by brine, dried over magnesium sulfate and evaporated to dryness under reduced pressure to yield 113.3 g (100% technical yield) of a red oil. Infrared (IR), nuclear magnetic resonance (NMR) and mass spectroscopy (MS) confirmed the structure as the desired product.

EXAMPLE II

Preparation of Methyl 2-Chloro-4-ethylthiobenzoate

In a round-bottom flask, 15 g (0.07 m) methyl 2-chloro-4-nitrobenzoate, 13.8 g (0.1 m) potassium carbonate, 5.4 g (0.09 m) ethanethiol and 250 ml acetone were combined and allowed to stir overnight. The acetone was removed under reducued pressure, the residue extracted with dichloromethane, treated with 2×150 ml water to remove salts, dried over magnesium sulfate and evaporated under reduced pressure to yield 14.6 g of an oil. No analyses were performed at this stage. The product of this reaction was converted to the benzoic acid by hydrolysis with sodium hydroxide and ethanol for identification by analysis of the benzoic acid. The structure was confirmed by IR, NMR and MS.

What is claimed is:
1. A method of preparing a compound of the formula

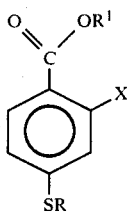

wherein R is alkyl, alkenyl, aryl or benzyl; R¹ is alkyl; and X is halogen or nitro comprising reacting a benzoate of the formula

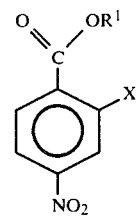

with a mercaptan of the formula R—SH in the presence of a polar aprotic solvent and an inorganic base.

2. A method according to claim 1 wherein R and R¹ are each $C_1$-$C_8$ alkyl and X is nitro.

3. A method according to claim 1 wherein R and R¹ are each $C_1$-$C_8$ alkyl and X is halogen.

4. A method according to claim 1 wherein R and R¹ are each $C_1$-$C_3$ alkyl and X is chlorine.

5. A method according to claim 1 wherein R and R¹ are both methyl and X is chlorine.

6. A method according to claim 1 wherein the solvent is a ketone.

7. A method according to claim 1 wherein the solvent is acetone.

8. A method according to claim 1 wherein the base is a phosphate.

9. A method according to claim 1 wherein the base is a carbonate.

10. A method according to claim 1 wherein the base is potassium carbonate.

* * * * *